US010500056B2

(12) United States Patent
Oster et al.

(10) Patent No.: US 10,500,056 B2
(45) Date of Patent: Dec. 10, 2019

(54) ATTACHMENT MEMBER AND CONNECTING MEMBER FOR A CARPOMETACARPAL THUMB JOINT PROSTHESIS AND CARPOMETACARPAL THUMB JOINT PROSTHESIS

(71) Applicant: SWEMAC INNOVATION AB, Linköping (SE)

(72) Inventors: Lars Oster, Lidköping (SE); Greg Packer, Hockley (GB)

(73) Assignee: SWEMAC INNOVATION AB, Linkoping (SE)

(*) Notice: Subject to any disclaimer, the term of this patent is extended or adjusted under 35 U.S.C. 154(b) by 595 days.

(21) Appl. No.: 15/101,419

(22) PCT Filed: Dec. 10, 2013

(86) PCT No.: PCT/SE2013/051478
§ 371 (c)(1),
(2) Date: Jun. 3, 2016

(87) PCT Pub. No.: WO2015/088403
PCT Pub. Date: Jun. 18, 2015

(65) Prior Publication Data
US 2016/0302935 A1  Oct. 20, 2016

(51) Int. Cl.
*A61F 2/42* (2006.01)
*A61F 2/46* (2006.01)
*A61F 2/30* (2006.01)

(52) U.S. Cl.
CPC ........ *A61F 2/4241* (2013.01); *A61F 2/30771* (2013.01); *A61F 2/4261* (2013.01);
(Continued)

(58) Field of Classification Search
CPC ............ A61F 2/4241; A61F 2002/4258; A61F 2002/4274; A61F 2002/4276;
(Continued)

(56) References Cited

U.S. PATENT DOCUMENTS 5,147,386 A   9/1992  Carignan et al.
5,522,903 A   6/1996  Sokolow et al.
(Continued)

FOREIGN PATENT DOCUMENTS

DE        4433483      5/1995
WO    2012121640      9/2012

*Primary Examiner* — Megan Y Wolf
(74) *Attorney, Agent, or Firm* — Tarolli, Sundheim, Covell & Tummino LLP

(57) ABSTRACT

The invention relates to an attachment member (2) and a connecting member (16) for a carpometacarpal thumb joint prosthesis (1) as well as to said thumb joint prosthesis. The attachment member (2) comprises a screw-like part (4) for attachment by screwing into the second metacarpal bone and a locking device (8) for locking the screw-like part to the connecting member (16). The connecting member comprises an elongated, arcuate element (16) which at one end portion (16a) thereof is configured with a hole (14) for connection to the attachment member (2) for the second metacarpal bone and which at the opposite end portion (16b) thereof is configured with a hole (15) for connection to an attachment member (3) for the first metacarpal bone. The joint prosthesis (1) comprises said attachment member (2) for the second metacarpal bone, an attachment member (3) with a screw-like part (5) for attachment by screwing into the first metacarpal bone and with an articulating ball element (6) as well as a corresponding articulating socket element (7), and said connecting member (16).

6 Claims, 10 Drawing Sheets

(52) U.S. Cl.
CPC ...... *A61F 2/4637* (2013.01); *A61F 2002/305* (2013.01); *A61F 2002/3054* (2013.01); *A61F 2002/3085* (2013.01); *A61F 2002/30331* (2013.01); *A61F 2002/30332* (2013.01); *A61F 2002/30367* (2013.01); *A61F 2002/30408* (2013.01); *A61F 2002/30507* (2013.01); *A61F 2002/30649* (2013.01); *A61F 2002/30881* (2013.01); *A61F 2002/30886* (2013.01); *A61F 2002/4256* (2013.01); *A61F 2002/4258* (2013.01); *A61F 2002/4276* (2013.01); *A61F 2002/4638* (2013.01)

(58) Field of Classification Search
CPC ...... A61F 2002/4256; A61F 2002/4271; A61F 2002/4279
See application file for complete search history.

(56) References Cited

U.S. PATENT DOCUMENTS

| | | | |
|---|---|---|---|
| 6,099,571 | A | 8/2000 | Knapp |
| 6,475,242 | B1 | 11/2002 | Bramlet |
| 6,485,520 | B1 | 11/2002 | Hubach et al. |
| 2005/0171613 | A1 | 8/2005 | Sartorius et al. |
| 2009/0254190 | A1 | 10/2009 | Gannoe et al. |
| 2011/0004255 | A1 | 1/2011 | Weiner et al. |
| 2011/0066153 | A1 | 3/2011 | Orbay et al. |
| 2011/0112652 | A1 | 5/2011 | Hansson et al. |
| 2013/0197655 | A1* | 8/2013 | Scheker ............... A61F 2/4241 623/21.16 |

\* cited by examiner

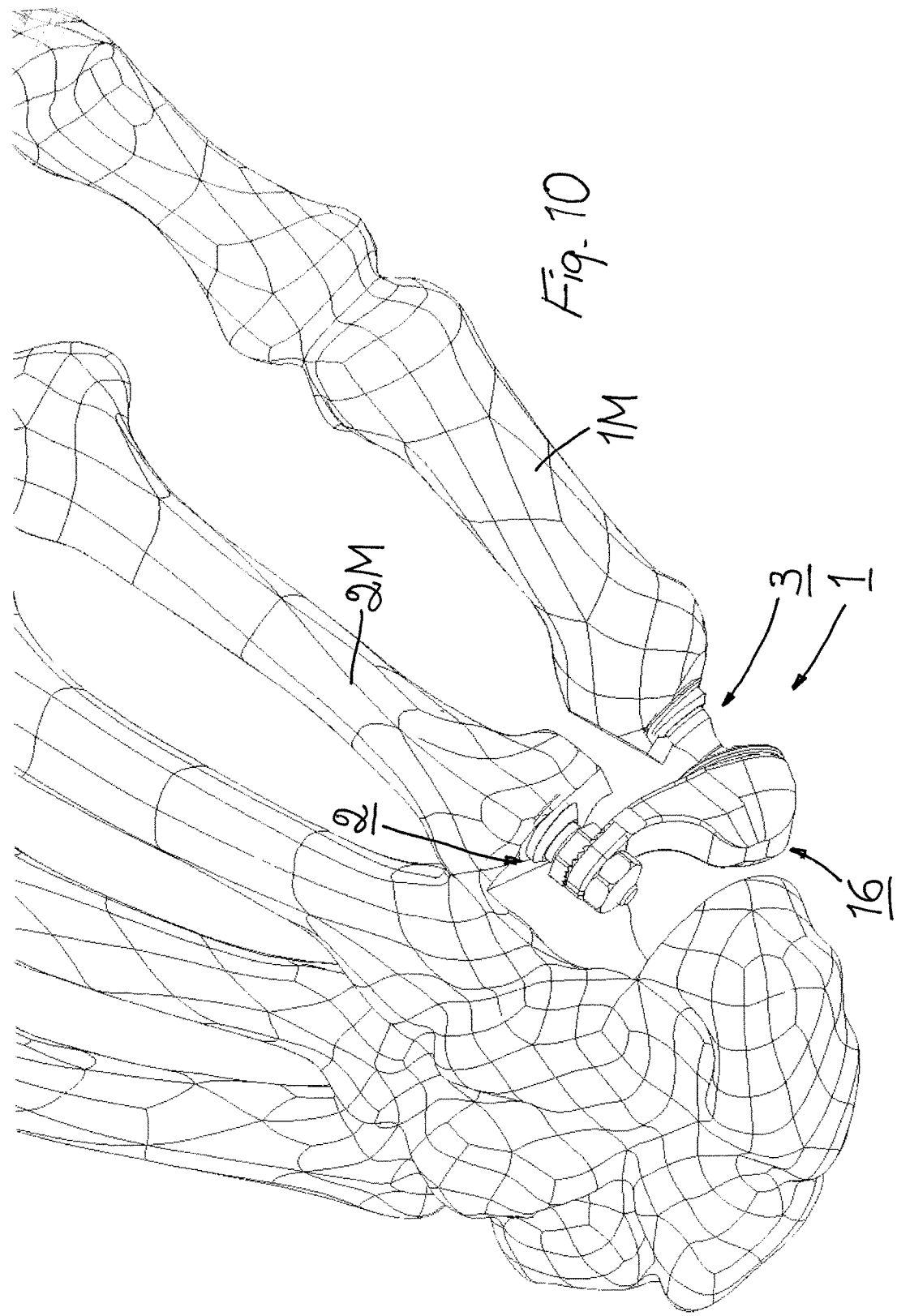

ATTACHMENT MEMBER AND CONNECTING MEMBER FOR A CARPOMETACARPAL THUMB JOINT PROSTHESIS AND CARPOMETACARPAL THUMB JOINT PROSTHESIS

RELATED APPLICATION

The application corresponds to PCT/SE2013/051478, filed Dec. 10, 2013, the subject matter, of which is incorporated herein by reference its entirety.

TECHNICAL FIELD

The present invention relates to an attachment member and a connecting member for a carpometacarpal thumb joint prosthesis as well as to said carpometacarpal thumb joint prosthesis.

BACKGROUND OF THE INVENTION

The joint prosthesis at which the attachment and connecting members according to the invention are configured for use, comprises two attachment members, of which one is configured for attachment to the second metacarpal bone and the other to the first metacarpal bone at a thumb joint, and a connecting member for connecting the two attachment members to each other. The attachment member for the second metacarpal bone comprises a screw-like part and the attachment member for the first metacarpal bone may comprise a screw-like part. These screw-like parts are adapted for being attached by screwing into the respective bone. The attachment members for the first and second metacarpal bones also comprise members for connecting the screw-like parts of the attachment members to the connecting member.

The above-mentioned type of joint prosthesis is configured for use as a primary replacement at thumb joints when the trapezium is not suitable for implantation, as an intra-operative salvage procedure when the trapezium is fractured and not suitable for implantation, as a salvage procedure after total trapezectomy or partial trapezectomy or other hemiarthroplasty or total replacement of another joint prosthesis or as a revision implant after loosening or failure of the screw-like part and/or the articulated socket element in the trapezium, i.e. for use after complete removal of the trapezium. The above-mentioned type of thumb joint prosthesis is configured for use also in patients having osteoarthritis, irrespective of the quality of the trapezium. The joint prosthesis is thereby replacing the normal interposition technique/conservative treatment.

At carpometacarpal thumb joint prosthesis, the attachment member for the second metacarpal bone is subjected to substantial bending and distraction forces, while the attachment member for the first metacarpal bone is subjected to substantial compression forces. It is important that the thumb joint prosthesis can be configured such that these forces can be met in order to achieve an effective and reliable joint prosthesis, i.e. the joint prosthesis can be configured to resist particularly said bending and distraction forces without breaking or loosening of any of its components.

SUMMARY OF THE INVENTION

Therefore, the object of the present invention is primarily to eliminate the problem that prosthesis members of the above-mentioned type are not configured to withstand the forces acting thereon when in use.

Accordingly, the attachment member according to the present invention comprises to this end a screw-like part which is configured for attachment by screwing into the second metacarpal bone and a locking device which is configured for locking the screw-like part to a connecting member of the thumb joint prosthesis for connecting the attachment member for the second metacarpal bone to an attachment member for the first metacarpal bone. The locking device of said attachment member comprises in turn a locking pin of which one end portion is attached to the screw-like part and of which the opposite end portion is configured for insertion into a hole in the connecting member, and a locking means which is configured for locking the locking pin to the connecting member. Said one end portion of the locking pin and the screw-like part may thereby be configured such that the locking pin is made in one piece with the screw-like part or said one end portion may alternatively be configured for insertion into a hole in the screw-like part for attaching the locking pin thereto.

The connecting member for use with the attachment member defined above comprises an elongated, substantially arcuate element which at one end portion thereof is configured with a hole for connection to said attachment member for the second metacarpal bone, and which at the opposite end portion thereof is configured with a hole for connection to an attachment member for the first metacarpal bone or, alternatively, with an articulating socket element for connection to an articulating ball element of an attachment member for the first metacarpal bone.

The above-mentioned attachment member and connecting member are used in a carpometacarpal thumb joint prosthesis, which except for said attachment member and connecting member also comprises an attachment member with a screw-like part which is configured for attachment by screwing into the first metacarpal bone at the thumb joint and with an articulating ball element as well as a corresponding articulating socket element. Alternatively, the screw-like part of the attachment member for the first metacarpal bone may be replaced by an unthreaded stem-like part which is inserted and attached to said first metacarpal bone in a suitable manner. This is possible because the forces applied onto the first metacarpal bone are no distraction forces that require such a stable and effective engagement in the bone as is required for the second metacarpal bone.

A carpometacarpal thumb joint prosthesis comprising an attachment member and a connecting member of improved construction and function as defined above, result in that the entire thumb joint prosthesis will work better and resist compression and particularly bending and distraction forces without breaking or loosening of any of its components.

BRIEF DESCRIPTION OF THE DRAWINGS

The above-mentioned and other objects of the invention, the characterizing features thereof and the advantages achieved thereby will be further described below with reference to the accompanying drawings, in which

FIG. 10 finally, illustrates with a schematic perspective view the assembled carpometacarpal thumb joint prosthesis after implantation thereof.

DETAILED DESCRIPTION OF PREFERRED EMBODIMENTS

Figure 1:
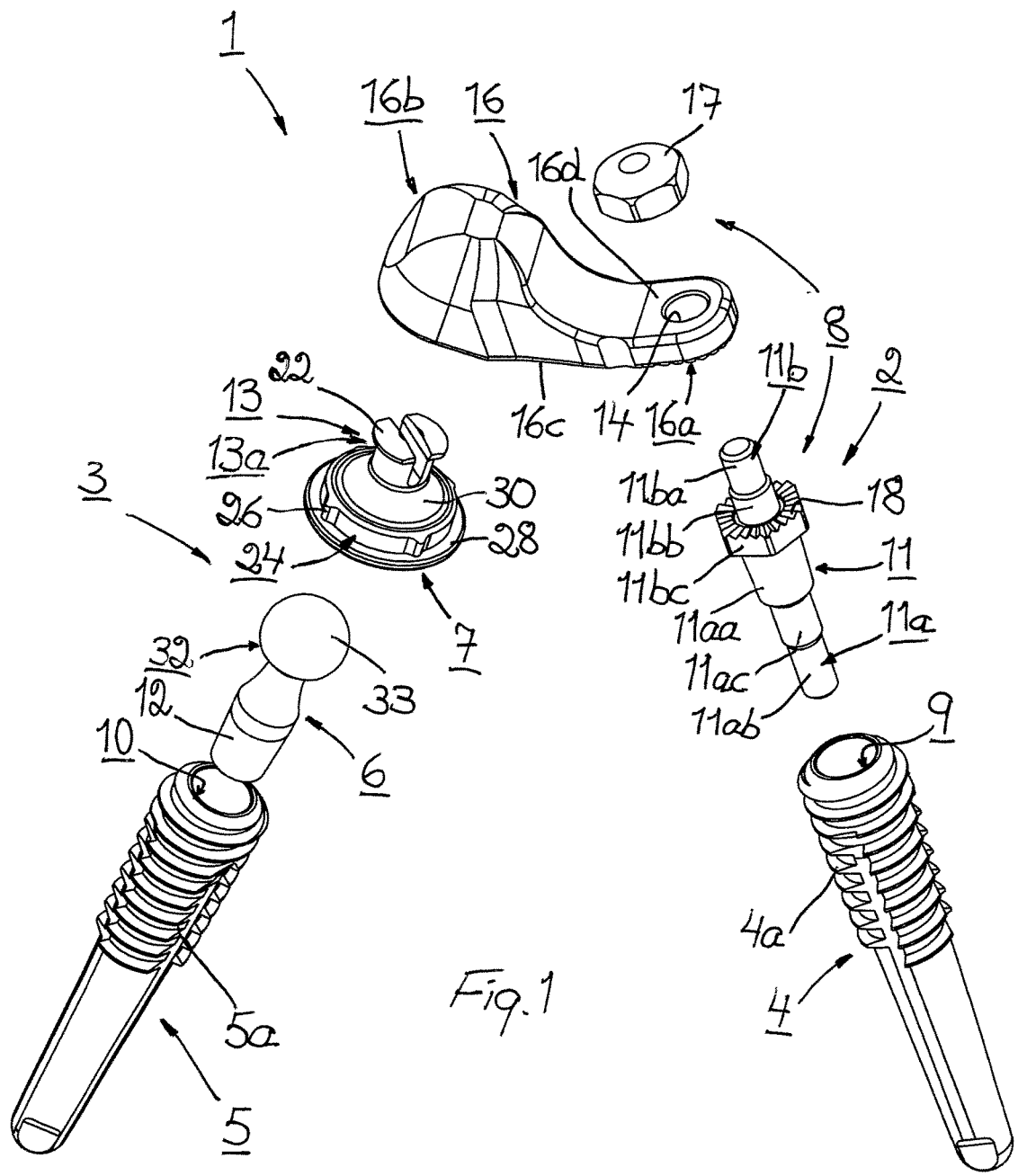
FIG. 1 is a schematic exploded perspective view from above of a carpometacarpal thumb joint prosthesis according to the present invention, comprising, inter alia, an attachment member and a connecting member according to the invention.

In the drawings, FIG. 1-6 illustrate a preferred embodiment of a carpometacarpal thumb joint prosthesis 1 according to the present invention. The thumb joint prosthesis 1 comprises, inter alia, two attachment members 2 and 3. One of the attachment members, in the illustrated embodiment attachment member 2, comprises a screw-like part 4 which is configured for attachment by screwing into the second metacarpal bone 2M. The other attachment member 3 also comprises a screw-like part 5 which is configured for attachment by screwing into the first metacarpal bone 1M at the thumb joint. The screw-like parts 4, 5 are for this purpose configured with threads 4a, 5a which entirely or partly extend in the longitudinal direction thereof. The attachment member 3 for the first metacarpal bone comprises also an articulating ball element 6 and, in the illustrated embodiment, an articulating socket element 7 for cooperation with the articulating ball element. The attachment member 2 according to the present invention for the second metacarpal bone 2M comprises also a locking device 8. The screw-like parts 4, 5 respectively, are in the illustrated embodiment provided with an attachment portion which consists of a hole 9 for the locking device 8 and a hole 10 for the articulating ball element 6 respectively. The locking device 8 comprises a locking pin 11 of which one end portion 11a is configured for insertion into the hole 9 in the screw-like part 4 for attaching the locking pin thereto and the articulating ball element 6 is configured with a mounting pin 12 which is insertable into the hole 10 in the screw-like part 5. The opposite end portion 11b of the locking pin 11 and a mounting pin 13 on the articulating socket element 7 are configured for insertion into holes 14 and 15 respectively, in a connecting member 16 of the joint prosthesis 1 for connecting the attachment member 2 for the second metacarpal bone 2M to the attachment member 3 for the first metacarpal bone 1M. The locking device 8 of the attachment member 2 for the second metacarpal bone 2M also comprises a locking means 17 which is configured for locking the locking pin 11 to the connecting member 16.

Figure 3:
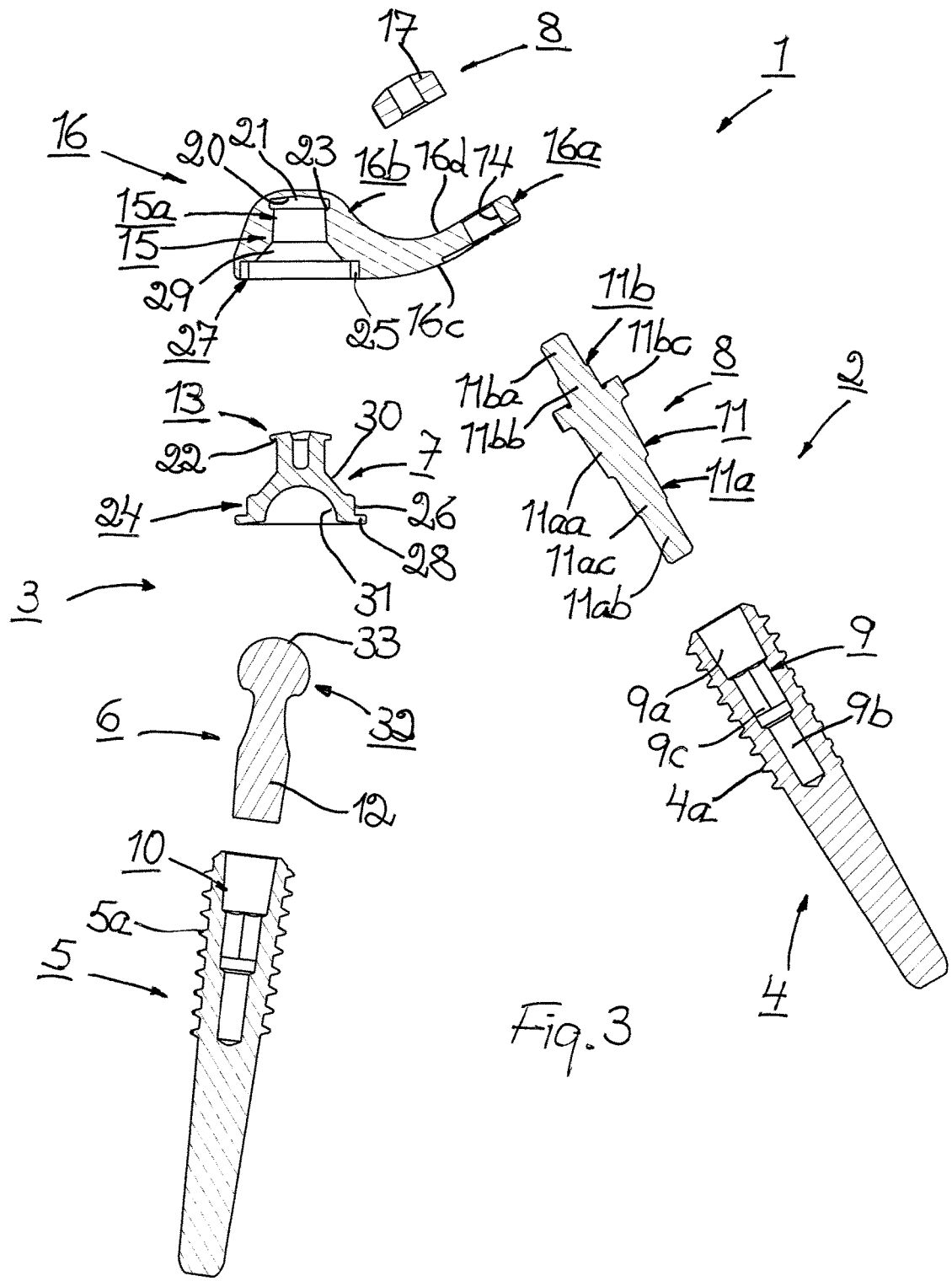
FIG. 3 is a schematic exploded sectional view of the thumb joint prosthesis of FIGS. 1 and 2.
Figure 4:
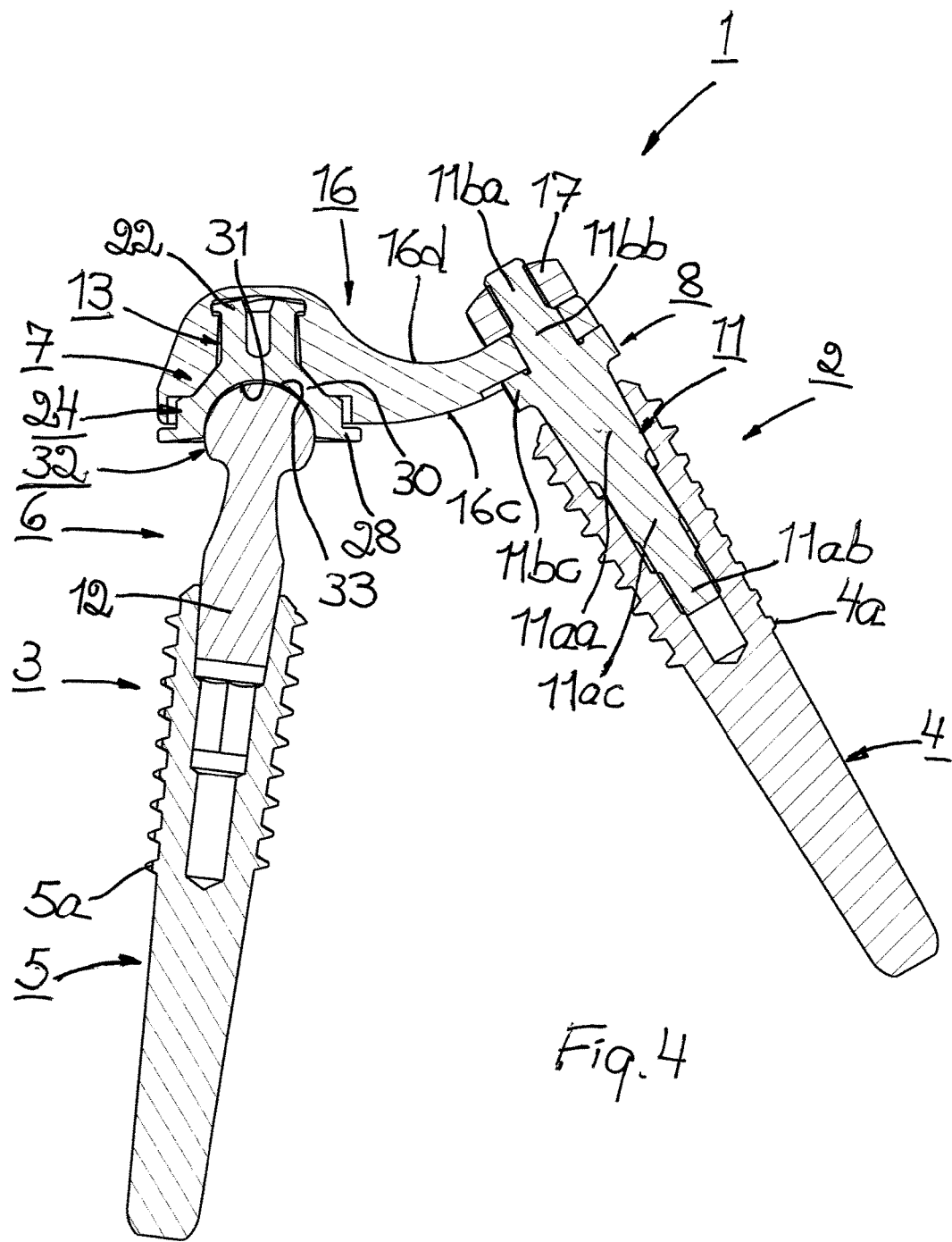
FIG. 4 is a schematic sectional view of the thumb joint prosthesis of FIGS. 1 to 3 after assembly thereof.
Figure 5:
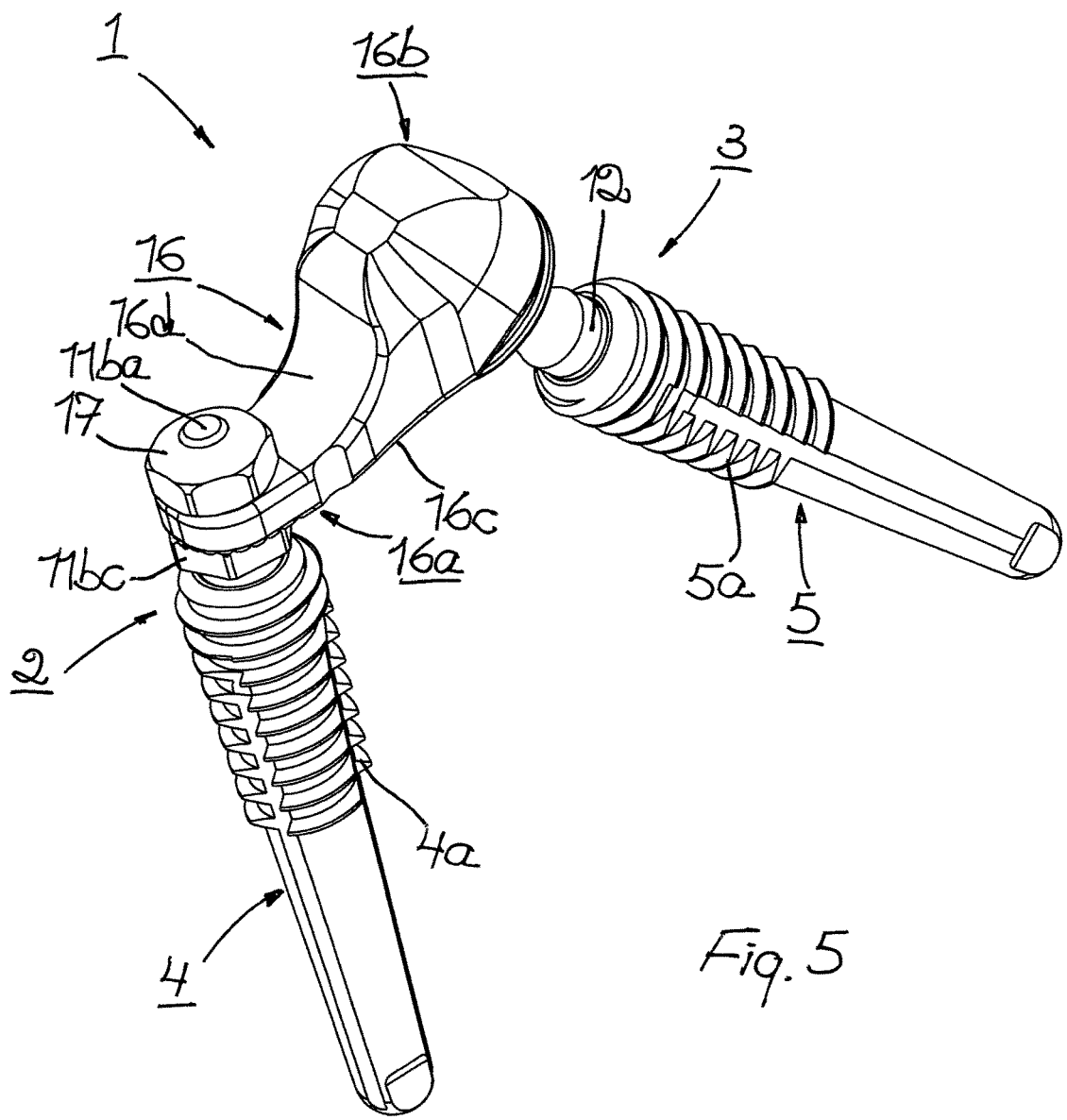
FIG. 5 is a schematic perspective view from above of the thumb joint prosthesis of FIGS. 1 to 3 after assembly thereof.
Figure 6:
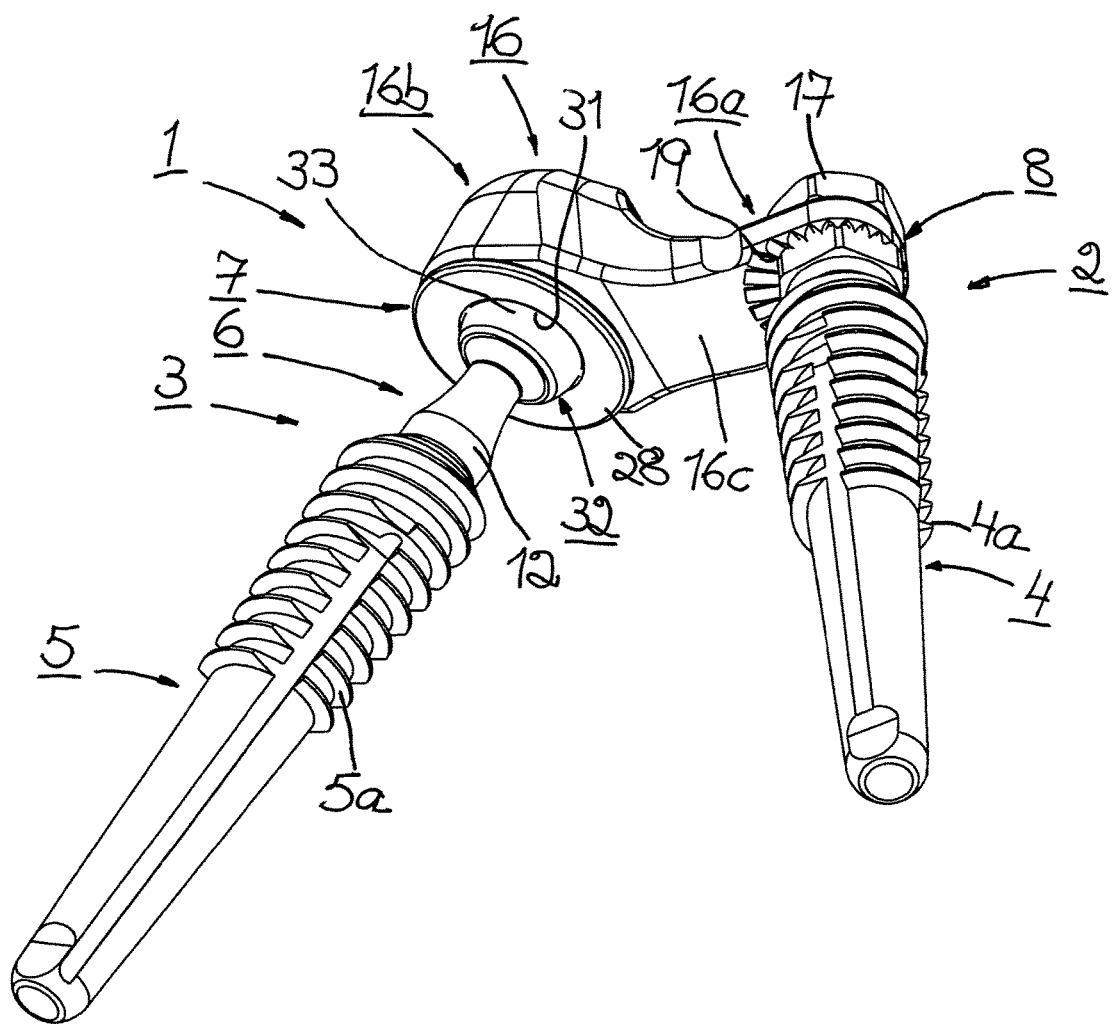
FIG. 6 is a schematic perspective view from below of the thumb joint prosthesis of FIGS. 1 to 3 after assembly thereof.

The hole 9 in the screw-like part 4 and said one end portion 11a of the locking pin 11 of the locking device 8 of the attachment member 2 for the second metacarpal bone 2M are configured with complementary portions 9a, 9b and 11aa, 11ab respectively, for attaching the locking pin to the screw-like part (see particularly FIG. 3). For being able to perform their function to resist bending and distraction forces applied thereto in an optimum manner, the hole 9 in the screw-like part 4 is configured with an outer, continuously, as in the illustrated embodiment, or stepwise conically tapering portion 9a and an inner, at least partly threaded portion 9b and said one end portion 11a of the locking pin 11 is configured with complementary conically tapering and threaded portions 11aa and 11ab respectively, for attaching the locking pin to the screw-like part. Thus, the complementary threaded portions 9b, 11ab of the hole 9 and locking pin 11 respectively, facilitate, as mentioned, carrying of distraction forces applied onto the second metacarpal bone 2M. In the illustrated embodiment, the conically tapering and threaded portions 11aa and 11ab of said one end portion 11a of the locking pin 11 are separated by an intermediate portion 11ac. The hole 9 in the screw-like part 4 is configured with a corresponding intermediate portion 9c between the conically tapering portion 9a and the threaded portion 9b, which portion comprises a seat for a screwing tool for attaching the screw-like part to the second metacarpal bone 2M. The hole 10 in the screw-like part 5 of the attachment member 3 for the first metacarpal bone 1M is in the illustrated embodiment identically configured.

The opposite end portion 11b of the locking pin 11 of the locking device 8 of the attachment member 2 for the second metacarpal bone 2M is for the same purpose, i.e. for facilitating carrying of distraction forces applied onto the second metacarpal bone, configured with a threaded portion 11ba for insertion into and through the hole 14 therefor in the connecting member 16 for engagement by a complementary threaded locking means 17 for locking the locking pin to the connecting member, i.e. said threaded portion extends out of said hole for engagement by the locking means. Adjacent to said threaded portion 11ba there is an unthreaded portion 11bb for insertion into said hole 14. This unthreaded portion 11bb remains in the hole 14 after insertion of said opposite end portion 11b of the locking pin 11 into said hole. Finally, a stop portion 11bc is provided adjacent to said unthreaded portion 11bb. This stop portion 11bc is in turn configured to engage the connecting member 16 around said hole 14 (see e.g. FIG. 4, 6 or 9). The locking means 17 is configured as a nut for threading onto the threaded portion 11ba of said opposite end portion 11b of the locking pin 11 until said nut engages the connecting member 16 and the stop portion 11bc of said opposite end portion of the locking pin engages the connecting member from two opposite sides. The stop portion 11bc of said opposite end portion 11b of the locking pin 11 is configured with setting means 18 for setting the connecting member 16 relative to the attachment member 2 by engagement with complementary setting means 19 around the hole 14 therefor in the connecting member. In the illustrated embodiment (see particularly FIGS. 1 and 2), these setting means 18, 19 are configured as radially extending serrations, allowing adjustment in e.g. about 15° intervals, but may of course be configured in any other manner suitable for their intended purpose.

The connecting member 16 according to the present invention comprises in the illustrated embodiment an elongated, substantially arcuate element which at one end portion 16a thereof is configured with the hole 14 for connection to the attachment member 2 for the second metacarpal bone 2M and which at the opposite end portion 16b thereof is configured with the hole 15 for connection to the attachment member 3 for the first metacarpal bone 1M. The elongated, substantially arcuate element 16 may have a bend of e.g. about 40°. The bend however, may alternatively be less or more than 40°.

The hole 14 in said one end portion 16a of the elongated, substantially arcuate element 16 which defines the connecting member, is configured as a through hole (FIGS. 3 and 4) for insertion therein from one side 16c of said arcuate element and locking on the opposite side 16d of said arcuate element of said opposite end portion 11b of the locking pin 11 of the locking device 8 of the attachment member 2 for the second metacarpal bone 2M. The hole 14 is on the insertion side 16c of said element 16 surrounded by the setting means 19 for setting the connecting member relative to the attachment member for the second metacarpal bone by engagement with the complementary setting means 18 on the opposite end portion 11b of the locking pin 11 of the locking device 8 of said attachment member 2.

The hole 15 in the opposite end portion 16b of the elongated, substantially arcuate element 16 is, as already mentioned above, configured for insertion therein of the mounting pin 13 of the articulating socket element 7 of the attachment member 3 for the first metacarpal bone 1M. The hole 15 is thereby configured with a portion 15a which together with a complementary portion 13a of the mounting pin 13 of the articulating socket element 7 permits fastening or fixation of the articulating socket element in said elongated, substantially arcuate element 16.

This means that the hole 15 can be configured to define e.g. a press fit with a complementary configured mounting pin 13 of the articulating socket element 7 such that the articulating socket element and the elongated, substantially arcuate element 16 can be brought to attach to each other by pressing them together. This is true particularly if both members 7, 16 are made of metal or a metal alloy, e.g. if the articulating socket element 7 is made of a CoCrMo-alloy.

If however, the articulating socket element 7 is made of e.g. a plastic material, e.g. PEEK (polyetheretherketon), which might be reinforced with carbon fibers, the complementary portions 13a, 15a may be configured differently. An articulating socket element of PEEK is illustrated in the drawings. At this latter embodiment, the hole 15 in the elongated, substantially arcuate element 16 may at the bottom 20 (see FIG. 3) be provided with a snap-in attachment 21 for the mounting pin 13 of the articulating socket element 7, because the mounting pin is configured with snap-in portions 22 which engage the snap-in attachment in the hole in said arcuate element. The snap-in attachment 21 in the hole 15 may be defined by a smaller extension of the hole in the parts thereof close to the bottom 20 of the hole, and the snap-in portions 22 on the mounting pin 13 are configured as hook-like parts. From the drawings, it is apparent that the mounting pin 13, in order to permit a snap-in connection thereof in the hole 15, is divided into two members with each a hook-like part 22. The mounting pin 13 may of course also be divided into more than two members and each such member may in turn have more than one hook-like part. The snap-in portions 22 configured as hooks on the mounting pin 13 of the articulating socket element 7, are brought together during insertion of the mounting pin in the hole 15, but move apart in the extended part 21 of the hole and prevent retraction of the articulating socket element by engaging the surface 23 defined by said extension and facing the bottom 20 of the hole.

The hole 15 in the elongated, substantially arcuate element 16 and a portion 24 of the articulating socket element 7 defining the socket, are also configured with complementary portions 25 and 26 respectively, which prevent rotation of the articulating socket element relative to said arcuate element.

Figure 2:
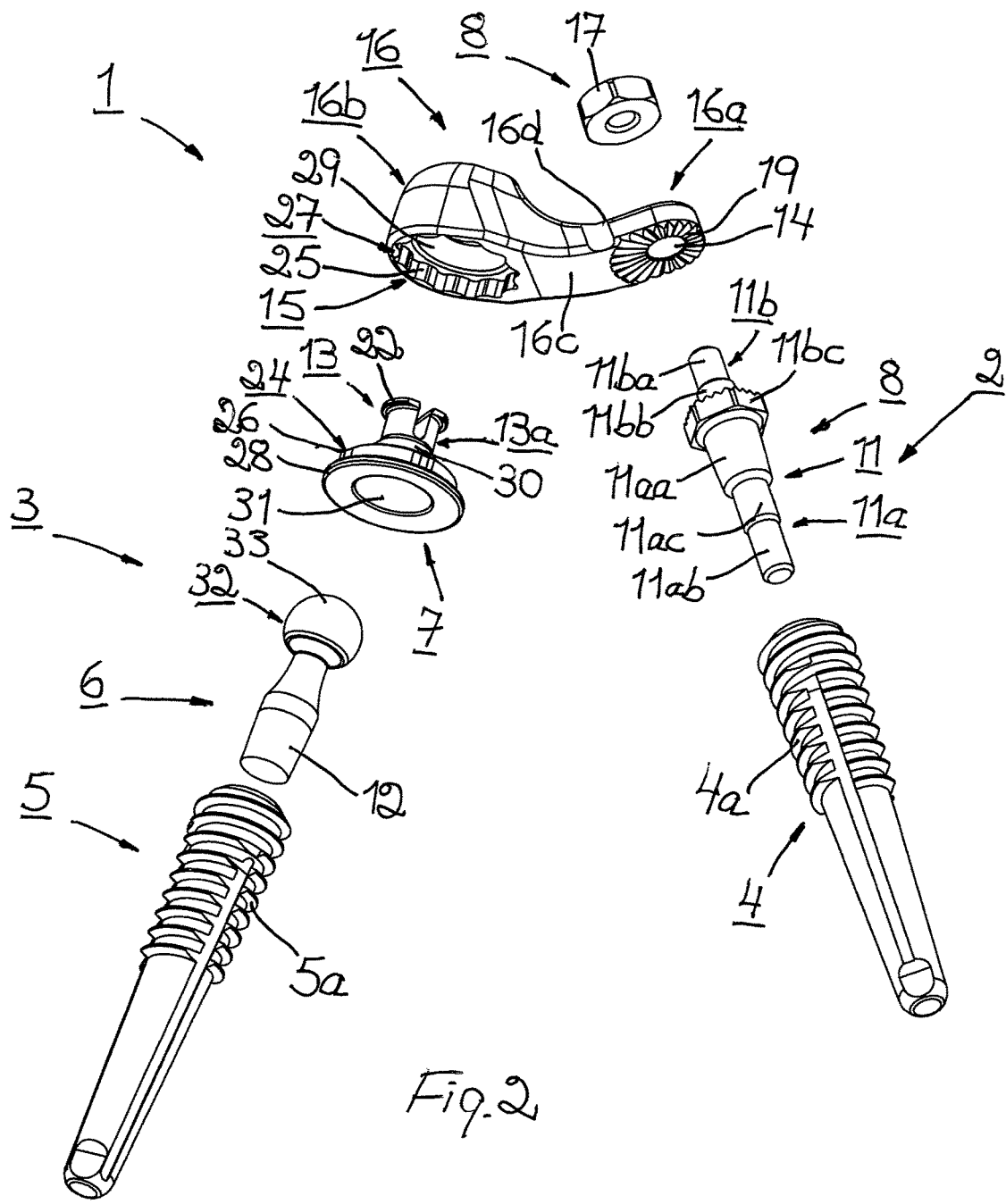
FIG. 2 is a schematic exploded perspective view from below of the thumb joint prosthesis of FIG. 1.

At the embodiment illustrated in the drawings (see particularly FIGS. 2 and 3), the hole 15 in the elongated, substantially arcuate element 16 is to this end on the inside of an opening 27 thereto provided with at least one recess 25 and the articulating socket member 7 has according to the drawings externally on the portion 24 defining the socket at least one protrusion 26 which engage the recess in said arcuate element. As is apparent from the drawings, said at least one recess on the inside of the opening 27 to the hole 15 may be configured as a number of recesses 25 uniformly distributed along said inside, e.g. twelve recesses (FIG. 2). The number of recesses 25 may vary and be more or less than twelve. From the drawings (particularly FIG. 1), it is also apparent that said at least one protrusion on the portion 24 may comprise four protrusions 26 uniformly distributed peripherally on the outside of said portion and having a curved side with substantially the same radius as the recesses 25. The number of protrusions 26 may also vary and be more or less than four, but not more than the number of recesses 25.

The articulating socket element 7 may further comprise, except for the mounting pin 13 and except for the portion 22 defining the socket and having at least one protrusion 26, a collar 28 on said portion. The object of this collar 28, which protrudes a little bit more over the side 16c of the elongated, substantially arcuate element 16 than said metallic articulating socket element, is, inter alia, to permit restoration without metalosis at a possible luxation. Since the articulating socket element 7 of metal is a bit lower, restoration at luxation is still easier than at older constructions.

Irrespective of which embodiment is used, the hole 15 in said opposite end portion 16b of the elongated, substantially arcuate element 16 may be conically shaped to thereby fit with a complementary, conically shaped mounting pin 13 of the articulating socket element 7. Alternatively, as illustrated in the drawings, the hole 15 in said opposite end portion 16b of the elongated, substantially arcuate element 16 may be configured with a conically shaped portion 29 to thereby fit with a complementary, conically shaped portion 30 between the mounting pin 13 and the portion 24 defining the socket of the articulating socket element 7 (see particularly FIG. 3). Another alternative is to make the elongated, substantially arcuate element 16 and the articulating socket element 7 in one piece, such that the attachment member 3 for the first metacarpal bone 1M thereby only comprises the screw-like part 5 and the articulating ball element 6. Also, said opposite end portion 16b of the arcuate element 16 is in the illustrated embodiment configured substantially as the trapezium in order to replace a totally removed trapezium and configure the joint prosthesis for optimum function. However, the opposite end portion 16b of the arcuate element 16 may have any other configuration suitable for its intended use and purpose.

As indicated above, the articulating socket element 7 comprises, in the illustrated embodiment, beyond the mounting pin 13, the portion 24 which defines a socket which in turn defines a concave joint or guide surface 31. The mounting pin 13 projects in an axial direction from the outer side of the portion 24 defining the socket and the conically shaped portion 30. The articulating ball element 6 comprises a substantially spherical ball 32 which defines a convex joint or guide surface 33 of such shape that it fits in the guide surface 31 of the articulating socket element 7 such that said guide surfaces 31, 33 can slide against each other and provide articulation of the joint. The mounting pin 12 on the articulating ball element 6 extends in an axial direction from the ball 32 and this mounting pin has a corresponding conical shape as the hole 10 in the screw-like part 5 of the attachment member 3 for the first metacarpal bone 1M. The shape and size of the mounting pin 12 on the articulating ball element 6 and the shape and size of the hole 10 in said screw-like part 5 may be selected such that they by moving them together in an axial direction can form a press fit between them. The shape and size of the mounting pin 12 on the articulating ball element 6 and the shape and size of the hole 10 in the said screw-like part 5 may also be selected such that they attach to each other in another way. It is also possible to make the second screw-like part 5 and the articulating ball element 6 in one piece.

The joint prosthesis described above can, in short, be assembled and implanted as follows:

After an incision has been made, the bones in question have been exposed and at least the trapezium resected, holes are drilled in the first and second metacarpal bones 1M, 2M using e.g. a guide wire and a cannulated drill.

Figure 7:
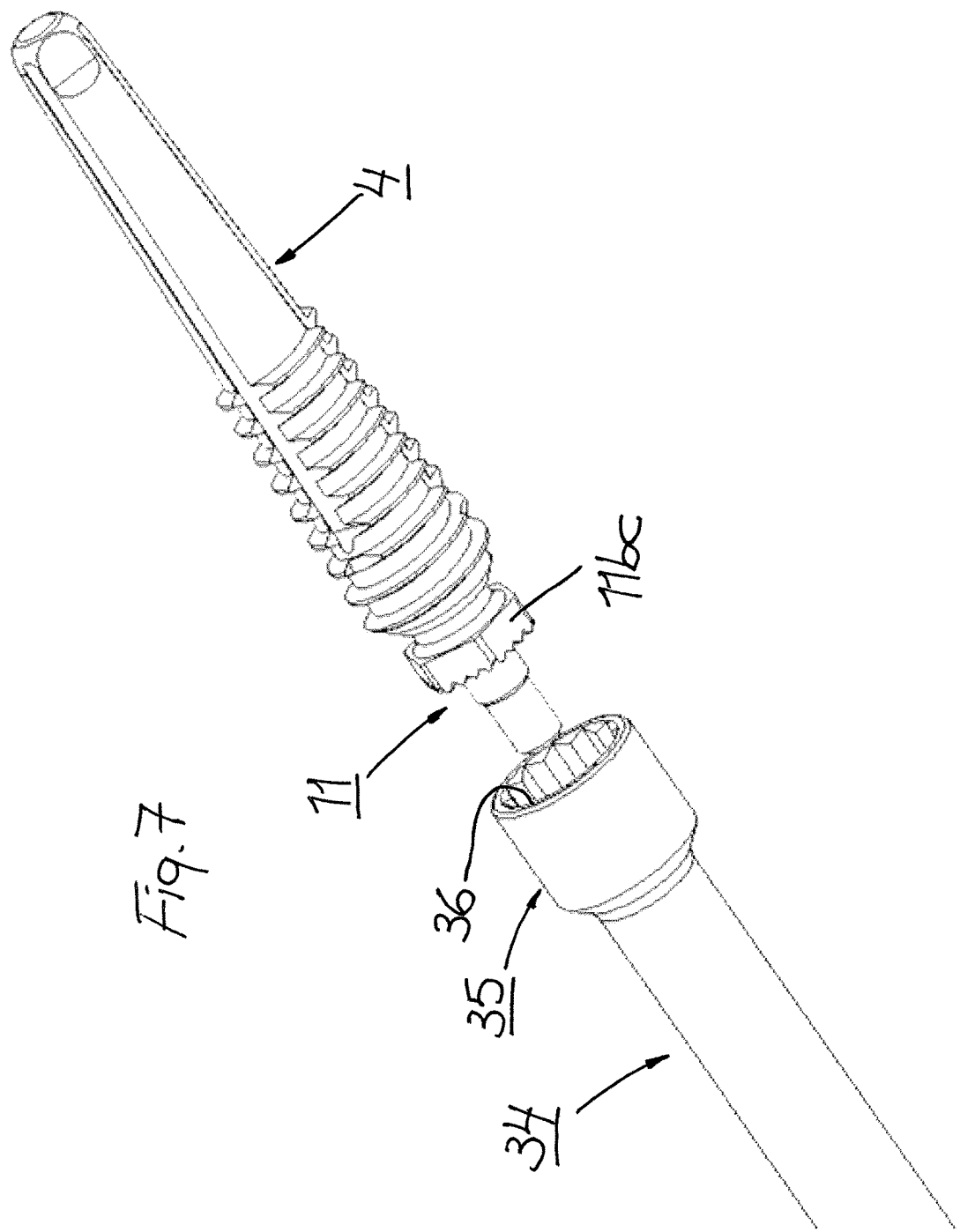
FIG. 7 is a schematic perspective view illustrating one way to assemble the attachment member according to the present invention.
Figure 8:
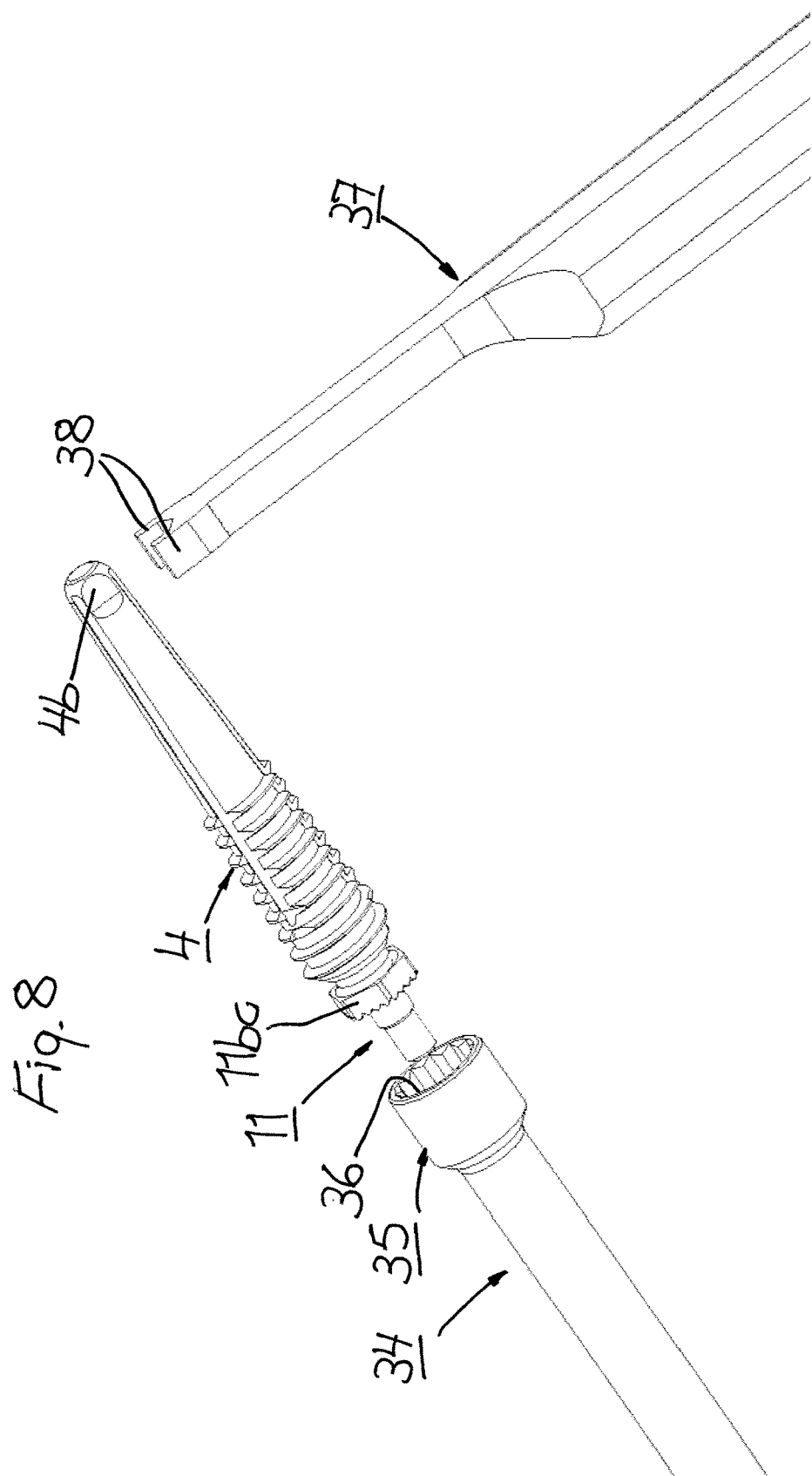
FIG. 8 is a schematic perspective view illustrating another way to assemble the attachment member according to the present invention.

The screw-like part 4 of the attachment member 2 for the second metacarpal bone 2M is attached by screwing into said bone, giving the screw-like part a good cortical fixation therein. Said one end portion 11a of the locking pin 11 of the locking device 8 is now inserted into the hole 9 in the screw-like part 4 and attached thereto by screwing. This is accomplished e.g. by means of the instrument 34 illustrated in FIG. 7, which instrument in one end thereof is provided with an enlarged portion 35 with an internal recess 36 which is configured for engagement of the complementary configured exterior of the stop portion 11bc of the locking pin 11. Alternatively, the end portion 11a of the locking pin 11 of the locking device 8 is inserted into and attached to the hole 9 in the screw-like part 4 before the screw-like part is screwed into the second metacarpal bone 2M. The screw-like part 4 may then be held by another instrument 37 illustrated in FIG. 8, preventing the screw-like part from rotating during insertion and attachment of the locking pin 11. The screw-like part 4 may to this end be configured with two opposed planar surfaces 4b at the tip thereof, which planar surfaces are engaged by two arms 38 of the instrument 37.

Figure 9:
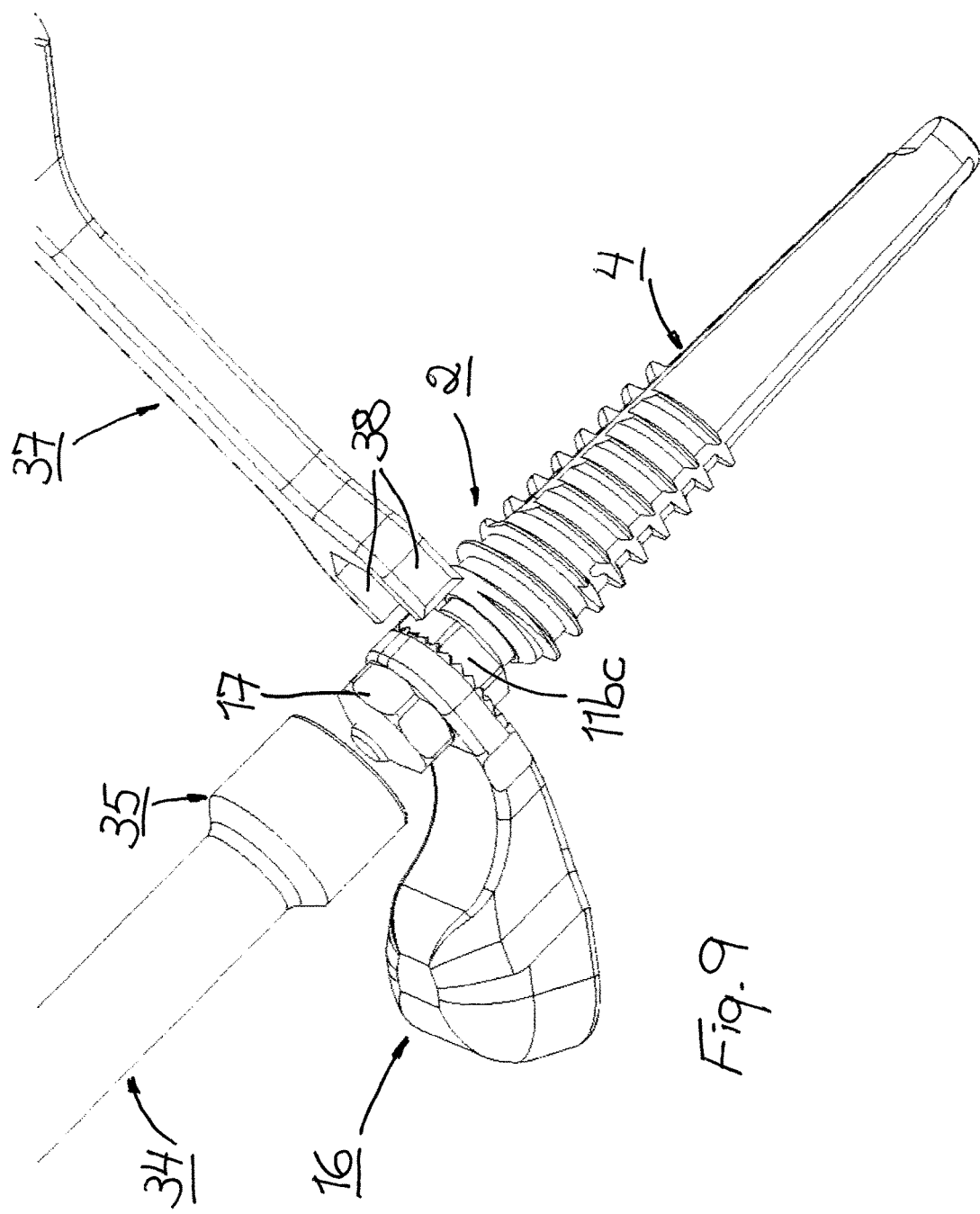
FIG. 9 is a schematic perspective view illustrating one way to assemble the attachment member and the connecting member according to the present invention.

The connecting member 16 is threaded onto the opposite end portion 11b of the locking pin 11, such that the threaded portion 11ba of said opposite end portion thereby extends through the hole 14 in said one end portion 16a of the elongated, substantially arcuate element forming the connecting member 16. The connecting member 16 is locked to the attachment member 2 by screwing the locking means 17 onto the part of the locking pin 11, i.e. the threaded portion 11ba of said opposite end portion 11b of the locking pin, projecting from the hole 14 in said one end portion 16a of the connecting member. After proper setting of the connecting member 16 relative to the attachment member 2, the locking means 17 is tightened and the connecting member 16 is thereby pressed against the attachment member and locked in the set position relative thereto. This is accomplished e.g. as illustrated in FIG. 9, by means of the same instrument 34 used for locking the locking pin 11 to the screw-like part 4, i.e. the internal recess 36 in the enlarged portion 35 of the instrument is now engaging the exteriorly complementary configured nut 17 of the locking device 8. During tightening, the instrument 37 illustrated in FIG. 8 for use as a holding-on tool for the screw-like part 4, may here be used also as a holding-on tool for the locking pin 11 and the screw-like part by bringing the arms 38 of said instrument to engage the complementary configured exterior of the stop portion 11bc of the locking pin. The screw-like part 4 is thereby prevented from being screwed further into the second metacarpal bone 2M.

The opposite end portion 16b of the elongated, substantially arcuate element forming the connecting member 16 will then, if configured as the trapezium, replace the entire trapezium and be seated where the trapezium otherwise would be located.

The articulating socket element 7 of the attachment member 3 for the first metacarpal bone 1M is inserted into the hole 15 in the opposite end portion 16b of the elongated, substantially arcuate element forming the connecting member 16, and the mounting pin 13 thereof is locked in said hole. Alternatively, the articulating socket element 7 of the attachment member 3 for the first metacarpal bone 1M can be inserted into the hole 15 in the opposite end portion 16b of the elongated, substantially arcuate element 16 and locked therein before said arcuate element is threaded onto the opposite end portion 11b of the locking pin 11 of the locking device 8 of the attachment member 2 for the second metacarpal bone 2M.

The screw-like part 5 of the attachment member 3 for the first metacarpal bone 1M is attached by screwing into said bone, giving the screw-like part a good cortical fixation therein.

The mounting pin 12 of the articulating ball element 6 of the attachment member 3 for the first metacarpal bone 1M is inserted into the hole 10 in the screw-like part 5 and locked therein, e.g. by a press-fit. Alternatively, the screw-like part 5 of the attachment member 3 for the first metacarpal bone 1M can be screwed into said bone and the mounting pin 12 of the articulating ball element 6 of said attachment member can be inserted into said screw-like part before the elongated, substantially arcuate element forming the connecting member 16, with or without the articulating socket element 7, is threaded onto the opposite end portion 11b of the locking pin 11 of the locking device 8 of the attachment member 2 for the second metacarpal bone 2M. With the attachment members 2, 3 in position in the first and second metacarpal bones 1M, 2M respectively, it is then possible to try out the best size of the connecting member 16 for optimum function, i.e. determine the distance between the first and second metacarpal bones, which of course will depend on e.g. the age and size of the patient. It is also important that the connecting member 16 is sufficiently low to prevent contact thereof with the distal part of the scaphoid bone, which sometimes can be affected by osteoarthritis.

Finally, the articulating ball element 6 and the articulating socket element 7 are brought together, the joint prosthesis is located properly and stability and range of motion is evaluated. Then, the wound is closed.

FIG. 10 illustrates the carpometacarpal thumb joint prosthesis 1 after implantation thereof.

It is obvious to a skilled person that the attachment member, connecting member and carpometacarpal thumb joint prosthesis according to the present invention can be modified and altered within the scope of the following claims without departing from the idea and purpose of the invention. Thus, the attachment of the locking device 8 to the screw-like part 4 may e.g. be configured differently and so may the connection of the connecting member 16 to the two attachment members 2, 3. The configuration of the locking device 8 and the connecting member 16 may also be different, i.e. the locking pin 11 and the locking means 17 may be configured in other ways and so may e.g. the holes 14, 15 in the connecting member in order to fit with said locking device and the articulating socket element 7 respectively. Also, although the embodiment of the carpometacarpal thumb joint prosthesis described above is advantageous in view of that identical screw-like parts can be used in the first as well as in the second metacarpal bone 1M, 2M, the screw-like part 5 for the first metacarpal bone can be replaced by an unthreaded stem-like part of prior art type, which is inserted into the bone and attached thereto e.g. by means of bone cement or by packing or hammering it in position. This unthreaded stem-like part may be configured with a hole similar to hole 10 in the screw-like part 5. The hole may alternatively, as may said hole 10, be configured to fit only with the mounting pin 12 of the articulating ball element 6. A further alternative is to reduce also the number of components of the attachment member 2 for the second metacarpal bone 2M by combining the screw-like member 4 and the locking pin 11 such that said one end portion 11a of the locking pin is attached to the screw-like part by making it integral therewith while said opposite end portion 11b is configured as defined above. Although not illustrated, said one end portion 11a may thereby be cut to such length that the stop portion 11bc of said opposite end portion 11b is located practically on the surface of the screw-like part 4 which otherwise is configured with the opening into the hole 9 in said screw-like part. Similarly, it is possible to reduce the number of components of the attachment member 3 for the first metacarpal bone 1M by combining the screw-like part 5, or the unthreaded stem-like part, and the articulating ball element 6 into one piece. Then, the length of the mounting pin 12 of the articulating ball element 6 is reduced in a similar way.

The invention claimed is:

1. Connecting member for a carpometacarpal thumb joint prosthesis,
   wherein the connecting member comprises an elongated, substantially arcuate element (16) which at one end portion (16a) thereof is configured with a hole (14) that is configured to receive an attachment member (2) for a second metacarpal bone (2M), and which at an opposite end portion (16b) thereof is configured substantially as a trapezium bone and configured with a hole (15) that is configured to receive an attachment member (3) for a first metacarpal bone (1M),
   wherein the hole (14) in said one end portion (16a) of the elongated, substantially arcuate element (16) is configured as a through hole for insertion therein from an insertion side (16c) of said elongated, substantially arcuate element and locking on an opposite side (16d) of said elongated, substantially arcuate element of an end portion (11b) of a locking pin (11) of a locking device (8) of the attachment member (2) for the second metacarpal bone (2M),
   wherein the hole (14) in said one end portion (16a) of the elongated, substantially arcuate element (16) is on the insertion side (16c) of said elongated, substantially arcuate element surrounded by setting means (19) for setting the connecting member relative to the attachment member (2) for the second metacarpal bone (2M) by engagement with complementary setting means (18) on said end portion (11b) of the locking pin (11) of the locking device (8) of said attachment member (2) for the second metacarpal bone (2M), and
   wherein the hole (15) in said opposite end portion (16b) of the elongated, substantially arcuate element (16) is configured for insertion therein of a mounting pin (13) of an articulating socket element (7) of the attachment member (3) for the first metacarpal bone (1M) and configured with a portion (15a) which together with a complementary portion (13a) of the mounting pin (13) of the articulating socket element (7) permits fastening of the articulating socket element in said elongated, substantially arcuate element.

2. Connecting member according to claim 1, wherein the hole (15) in said opposite end portion (16b) of the elongated, substantially arcuate element (16) comprises a snap-in attachment (21) for engagement by complementary snap-in portions (22) on the mounting pin (13) of the articulating socket element (7).

3. Connecting member according to claim 1, wherein the hole (15) in said opposite end portion (16b) of the elongated, substantially arcuate element (16) is configured with a portion (25) which together with a complementary portion (26) of a portion (24) defining a socket of the articulating socket element (7) prevents rotation of the articulating socket element relative to said elongated, substantially arcuate element.

4. Connecting member according to claim 3, wherein the hole (15) in said opposite end portion (16b) of the elongated, substantially arcuate element (16) is on an inside of an opening (27) to said hole configured with at least one recess (25) for engagement by at least one complementary protrusion (26) externally on the portion (24) defining the socket of the articulating socket element (7) to prevent rotation of the articulating socket element relative to said elongated, substantially arcuate element.

5. Connecting member according to claim 1, wherein the hole (15) in said opposite end portion (16b) of the elongated, substantially arcuate element (16) is conically shaped to fit with a conically shaped mounting pin (13) of the articulating socket element (7).

6. Carpometacarpal thumb joint prosthesis, comprising:
   the connecting member (16) according to claim 1,
   an attachment member (2) with a screw-like part (4) which is configured for attachment by screwing into a second metacarpal bone (2M) at a thumb joint, and with a locking device (8) which comprises a locking pin (11) of which one end portion (11a) is configured for insertion into a hole (9) in the screw-like part (4) and of which an opposite end portion (11b) of the locking pin (11) is configured for insertion into the hole (14) in said one end portion (16a) of the connecting member (16), and a locking means (17) which is configured for locking the locking pin (11) to the connecting member (16), and
   an attachment member (3) with a screw-like part (5) which is configured for attachment by screwing into a first metacarpal bone (1M) at the thumb joint, and with an articulating ball element (6) which is connected to said screw-like part (5) as well as a corresponding articulating socket element (7) of which a mounting pin (13) is insertable into the hole (15) in said opposite end portion (16b) of the connecting member (16) for fastening of the articulating ball element (6) to the connecting member (16).

* * * * *